United States Patent
Muni

[19]

[11] Patent Number: 5,853,408

[45] Date of Patent: Dec. 29, 1998

[54] IN-VIVO MODIFICATION OF THE MECHANICAL PROPERTIES OF SURGICAL DEVICES

[75] Inventor: Ketan P. Muni, San Jose, Calif.

[73] Assignee: Advanced Cardiovascular Systems, Inc., Santa Clara, Calif.

[21] Appl. No.: 457,325

[22] Filed: Jun. 1, 1995

Related U.S. Application Data

[63] Continuation-in-part of Ser. No. 242,410, May 13, 1994, abandoned, which is a continuation of Ser. No. 932,607, Aug. 20, 1992, abandoned.

[51] Int. Cl.⁶ ..................................................... A61N 5/00
[52] U.S. Cl. ............................. 606/27; 604/96; 604/200; 606/192
[58] Field of Search ................................ 606/27, 28, 192, 606/194; 604/94, 280–281

[56] References Cited

U.S. PATENT DOCUMENTS

| | | |
|---|---|---|
| Re. 32,983 | 7/1989 | Levy . |
| Re. 33,561 | 3/1991 | Levy . |
| 3,524,447 | 8/1970 | Evans . |
| 4,176,662 | 12/1979 | Frazer . |
| 4,385,635 | 5/1983 | Ruiz . |
| 4,490,421 | 12/1984 | Levy . |
| 4,577,543 | 3/1986 | Wilson . |
| 4,624,657 | 11/1986 | Gould et al. . |
| 4,790,831 | 12/1988 | Skribiski . |
| 4,860,744 | 8/1989 | Johnson et al. . |
| 4,963,306 | 10/1990 | Weldon . |
| 5,035,694 | 7/1991 | Kasprzyk et al. . |
| 5,037,404 | 8/1991 | Gold et al. . |
| 5,078,736 | 1/1992 | Behl . |
| 5,098,429 | 3/1992 | Sterzer . |
| 5,114,423 | 5/1992 | Kasprzyk et al. . |
| 5,151,100 | 9/1992 | Abele et al. . |
| 5,168,880 | 12/1992 | Sogawa et al. . |
| 5,178,620 | 1/1993 | Eggers et al. . |
| 5,188,602 | 2/1993 | Nichols . |
| 5,190,540 | 3/1993 | Lee . |
| 5,195,965 | 3/1993 | Shantha . |
| 5,280,130 | 1/1994 | Markle et al. . |
| 5,304,340 | 4/1994 | Downey .................................... 606/194 |
| 5,344,398 | 9/1994 | Hara . |
| 5,344,400 | 9/1994 | Kaneko et al. .......................... 606/192 |
| 5,346,508 | 9/1994 | Hastings .................................... 607/99 |
| 5,368,591 | 11/1994 | Lennox et al. . |
| 5,441,489 | 8/1995 | Utsumi et al. ........................... 604/280 |

FOREIGN PATENT DOCUMENTS

| | | |
|---|---|---|
| A-41 005 660 | 7/1992 | Japan . |
| A-42 000 565 | 11/1992 | Japan . |

*Primary Examiner*—Robert L. Nasser
*Attorney, Agent, or Firm*—Fulwider Patton Lee & Utecht

[57] ABSTRACT

The mechanical properties of various angioplastic surgical devices are altered in order to enhance their transportability through the vascular system by changing their operating temperature while situated within the body. Temperature increases are utilized to increase flexibility or cause devices to assume certain configurations while a temperature decrease serves to increase stiffness and rupture strength.

16 Claims, 4 Drawing Sheets

IN-VIVO MODIFICATION OF THE MECHANICAL PROPERTIES OF SURGICAL DEVICES

This application is a continuation-in-part of U.S. Ser. No. 08/242,410 filed May 13, 1994, now abandoned which is a continuation of U.S. Ser. No. 07/932,607 filed Aug. 20, 1992, now abandoned.

BACKGROUND OF THE INVENTION

1. Field of the Invention

The present invention relates generally to angioplastic procedures and more particularly pertains to surgical devices that are introduced into and advanced through the vascular system during angioplastic procedures.

2. Description of the Prior Art

A variety of devices are employed in modern angioplastic techniques that are intended for introduction into and advancement through a patient's vasculature. Such devices include guidewires, various catheter type structures, retrieval devices, stents, etc. An important criterion inherent in the design and construction of such devices is the ability of the device to be easily advanced through vessels to the operative site and furthermore, to provide such "transportability" without compromising the ability of the device to perform its intended function once in position. The relatively small diameter of the vessels through which such devices are routinely passed and the potentially long and tortuous paths such devices may be forced to follow renders certain mechanical properties of such devices of critical importance.

The rigidity of an intravascular device is a representative example of a mechanical property of crucial import vis-a-vis the transportability of the device. The pushability, torqueability, and trackability of an elongated structure are all affected by the inherent rigidity of that structure. A guidewire or catheter must, for example, have sufficient rigidity to enable its distal end to be maneuvered by manipulation of its proximal end. Conversely, such device must be sufficiently flexible to enable it to follow a circuitous path and to prevent injury to the vessel walls.

The cross-sectional dimensions or profile of an intravascular device are dictated by the size of the vessels through which the device is to be advanced. In the case of balloon catheters, the mechanical properties of the materials employed in the device's construction play an important role in the ability of the device to be initially constrained to a sufficiently small profile in order to facilitate its advancement from the point of introduction to the operative site, to readily assume a substantially larger size upon expansion at the operative site, and to subsequently reassume the initial small profile for unrestricted extraction from the patient. It is therefore essential to select a material for the construction of a balloon that is flexible, strong and has a "memory."

Some of these seemingly mutually exclusive requirements have been previously addressed by innovative approaches. With respect to the above-described requirements for guidewires or catheters to be rigid for some purposes yet simultaneously flexible for other reasons, it was recognized that a flexible distal end matched with a relatively rigid body element would substantially enhance the transportability of such a device. However, the utility of such an approach is nonetheless limited as situations inevitably will be encountered where the distal end of a particular device is either too stiff to be forced through a small radius bend, or too flexible to allow its position to be properly controlled. Furthermore, a very flexible tip may be necessary in order to reach a targeted stenosis, while substantially more stiffness may be required in order to cross through the stenosis if particularly occluded.

With regard to the above-described problems vis-a-vis the profile of balloon catheters, it has been found that by folding the balloon material into certain configurations a smaller deflated profile can be achieved for a given inflated size. However, the balloon's ultimate strength and the ability of a balloon to "remember" its folded shape typically are properties that are in conflict with one another, i.e. the stronger, more rupture-resistant the material, the weaker its memory.

The transportability of a prior art intravascular device may be hindered under certain conditions by the very mechanical properties of the materials employed in its construction that serve to enhance the device's transportability under a different set of conditions. Similarly, those mechanical properties of the materials that optimize the device's intended performance once in position may severely compromise its transportability. The prior art has provided for only limited improvements in this regard by typically employing either a specializing approach, i.e., by optimizing relevant parameters to fit a specific situation, or a compromising approach, i.e., providing somewhat compromised performance but for a wider range of situations. The capability for adapting a specific angioplastic device to different situations at different times has not been provided by the prior art. The present invention satisfies this need.

SUMMARY OF THE INVENTION

The present invention serves to substantially enhance the transportability of intravascular devices by providing for the controllable variation of some of the mechanical properties of such devices while situated within a patient's vasculature. This is achieved by employing carefully selected materials in the construction of critical components or regions of an intravascular device and by providing means therein for remotely varying its operating temperature. The materials are selected to have certain mechanical properties that change as their temperature is varied between limits tolerable within the body. The present invention encompasses both the cooling as well as the heating of the device by a variety of means while it is situated within the patient. Moreover, the invention is adaptable to many different intravascular devices.

A balloon or other expandable element constructed in accordance to the present invention will be somewhat distensible in at least its expanded diameter. The balloon diameter, when fully expanded under 6–12 atm. of pressure, will increase by 3% to 6%, or more, when heated to temperatures ranging from 37° C. to 70° C. The increase in balloon diameter is achieved without increasing pressure, thus reducing the likelihood of injuring the vessel or pressurizing the balloon up to its burst pressure. Further, upon deflation, the heated balloon more readily collapses to its folded, preinflated configuration and it is also far less likely to pancake or flatten upon deflation. In other words, the heated balloon of the present invention will fold back to its originally folded configuration much more easily than if it is unheated.

A guidewire, guiding catheter or catheter constructed according to the present invention has a distal end formed of material selected to become increasingly flexible with increased temperature. The material is further selected to display a desirable range of stiffness within the range of temperatures tolerable within the body. The present invention provides for a variety of ways to controllably increase the temperature of the distal end while situated within the vascular system. In a preferred embodiment, a lumen formed within certain angioplastic devices is employed to conduct heated fluid to and from selected regions of the device wherein an increased temperature is desired. As an alternative, light energy is conducted to the distal end via an optical fiber where it is absorbed by material forming the distal end.

In another preferred embodiment, a portion of tubing suitable for use as a catheter, balloon material, guiding catheter, guidewire, or other similar device, is made from a polymeric material such as PET (polyethylene teraphthalate), Nylon 12, LLDPE (linear low density polyethylene), HDPE (high density polyethylene), and surlyn ionomer. The tubing is heated in the range of 20° C. to 100° C. to selectively increase its flexibility at one or more points along its length, including at its distal tip. Thus, the present invention provides a catheter, for example, that can become more flexible while it is being inserted and routed through a tortuous vessel so that it can more easily traverse the vessel and reduce the likelihood of damage to the vessel wall.

The present invention additionally, optionally provides for the cooling of selected portions of surgical devices either to lower their operating temperature to below ambient or to more rapidly reduce their previously elevated temperature. This is accomplished either by conducting cooled fluid or gas to and from the selected region of the surgical device, allowing a liquid conducted thereto to undergo a phase change or allowing a compressed gas conducted thereto to expand. Thus, when pushing a balloon through a highly restricted coronary artery, the present invention provides a stiffer catheter (due to cooling) having greater pushability and torqueability, with somewhat less flexibility. These desired features are provided by selectively controlling the temperature of the tubing as described.

The temperature of the region of the device subject to heating and/or cooling is optionally monitored. A thermocouple, an optical sensor or a resistance device, for example, is readily adaptable to provide a real time, accurate indication of the temperature of a specific component or region of the surgical device while situated within the vascular system. The sensed temperature data is further optionally utilized in a closed loop control system to facilitate an automatic control of a desired set temperature.

During the angioplastic procedure, the progress of the distal end of the device through the vascular system is monitored in the conventional manner. In the case of a guidewire or catheter, when additional flexibility is required in order to negotiate a particularly circuitous path, the temperature of the device is increased. Conversely, when more pushability is required of the device, its temperature is allowed to decrease back down to ambient or is actively reduced by cooling means. In the case of a foldable balloon catheter, upon completion of the dilatation of the targeted artery, the balloon is collapsed and its temperature is increased to facilitate its folding after which the device is more easily extracted from within the vascular system.

These and other features and advantages of the present invention will become apparent from the following detailed description of the preferred embodiments which, taken in conjunction with the accompanying drawings, illustrates by way of example the principles of the invention.

DETAILED DESCRIPTION OF THE PREFERRED EMBODIMENTS

The Figures illustrate various embodiments of the present invention. Each embodiment comprises an medical device which is inserted into a patient, generally into the vascular system, maneuvered to the operative site, and ultimately removed at the conclusion of the procedure. The present invention provides for an enhancement of the transportability of such devices throughout the vascular system.

Figure 1:
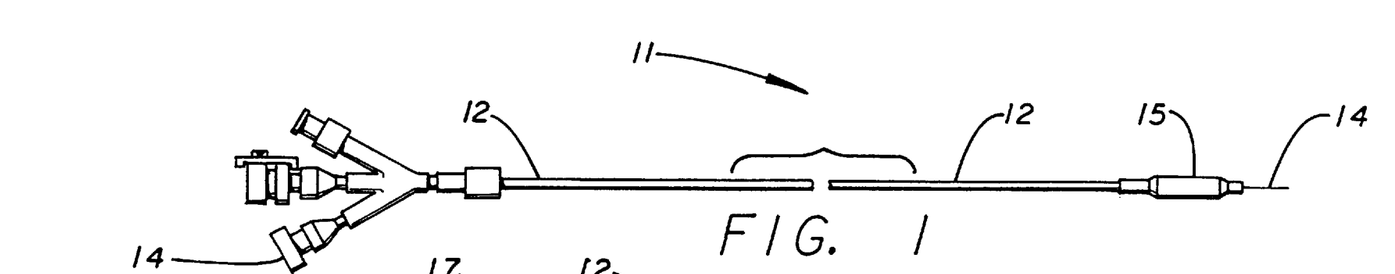
FIG. 1 is a schematic view of a balloon catheter assembly incorporating aspects of the invention.
Figure 2:
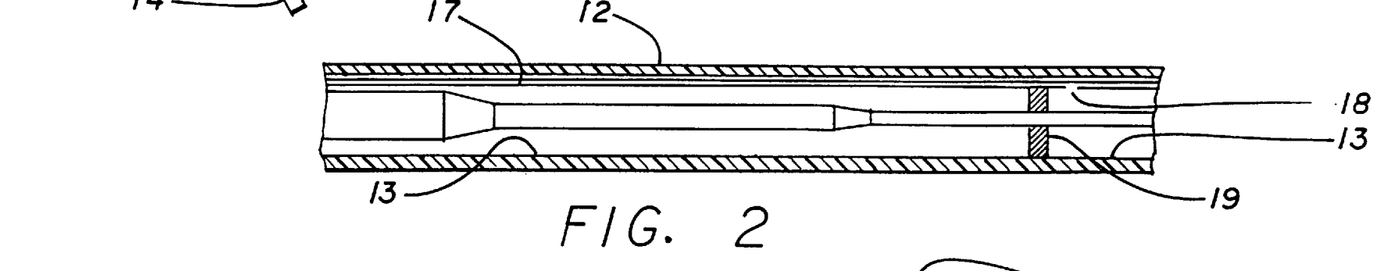
FIG. 2 is a longitudinal, partial cross-sectional view of the catheter shaft of FIG. 1.
Figure 3:
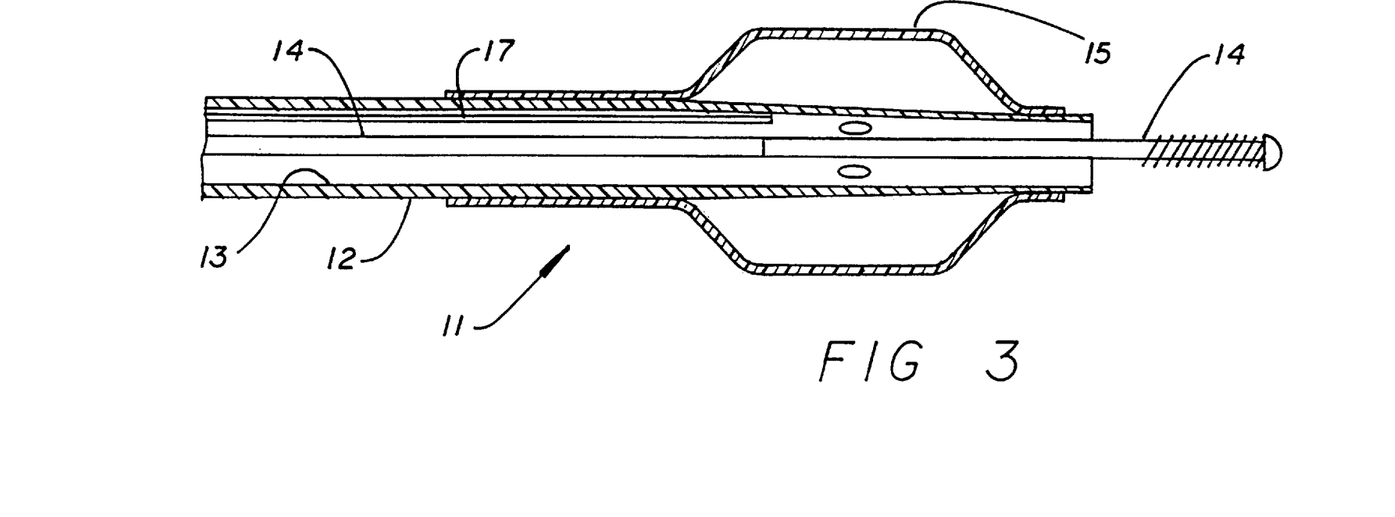
FIG. 3 is a longitudinal cross-sectional view of the distal end of the catheter assembly of FIG. 1, including the balloon portion.

In keeping with the invention, as shown in FIGS. 1–3, a conventional angioplasty catheter assembly 11 is depicted. With this type of assembly, a typical angioplasty procedure can be performed, such as a percutaneous transluminal coronary angioplasty (PTCA). Such procedures are routine and are described in U.S. Pat. Nos. 4,771,778; 4,323,071; 4,468,224; and 4,573,470, which are incorporated herein by reference.

The catheter assembly 11 includes a catheter shaft 12 having an inner lumen 13. A guidewire 14 is slidably housed in inner lumen 13 and it assists in positioning the catheter shaft 12 in a patient's vessel. The catheter shaft 12 will slide over the in-place guidewire 14 to position balloon 15 located on the distal end of catheter shaft 12. This assembly is commonly referred to as an over-the-wire delivery system, however, the present invention is equally applicable to other known delivery systems such as fixed-wire, rapid-exchange, and monorail-type catheter systems.

In a typical PTCA procedure, the balloon 15 is positioned in the patient's coronary artery where a stenosed area exists. The balloon 15 is expanded using fluid pressure on the order of 8–15 atmospheres for short periods of time, i.e., 10–20 seconds. After the stenosed area is opened to blood flow, the balloon is deflated and catheter shaft 12 and balloon 15 are withdrawn from the patient, as is guidewire 14.

In keeping with the invention, catheter shaft 12 must be flexible enough to navigate through tortuous blood vessels and coronary arteries, yet must also be torqueable and pushable to cross narrowed and restricted arteries. Further, such catheters 12 must be able to track over a guidewire with minimal resistance. It is also important that the balloon deflate into a low profile shape that approximates its preinflated shape. The present invention solves the problems discussed.

Figure 4:
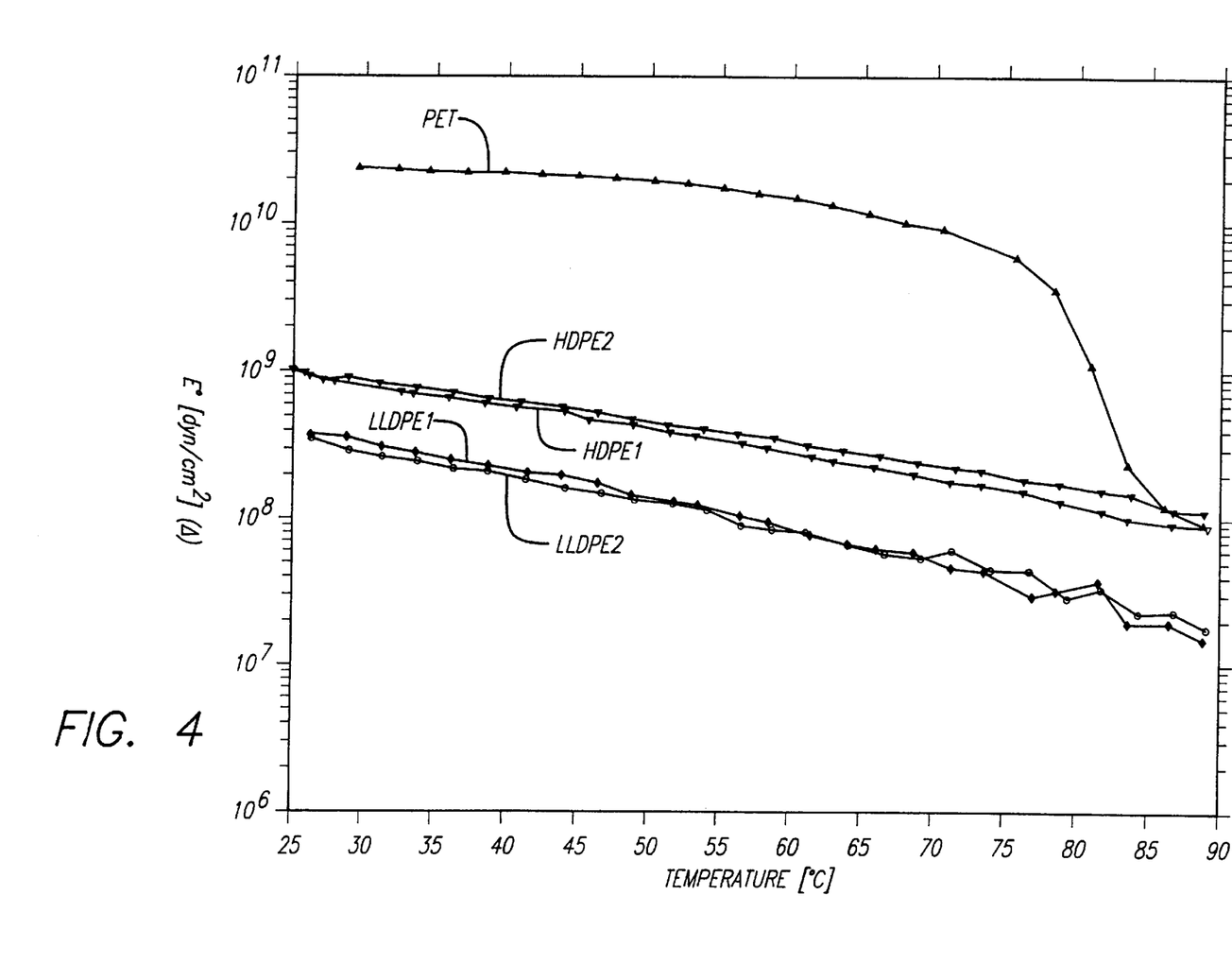
FIG. 4 is a graph representing the test data of Table I.

The test results are reproduced in Table I for various polymeric materials. In order to more clearly demonstrate the increased flexibility of the tubing due to heating, the E' values were plotted in Graph I of FIG. 4.

TABLE I

| Material | Extrusion Number | Irradiation Dose, mRad | Effective Radius, mm | Frequency Rad/sec | E', Dynes/sq cm(x10E8) 37° C. | 50° C. | 70° C. |
|---|---|---|---|---|---|---|---|
| PET | 11-241-A | 0 | 0.433 | 6.28 | 220.0 | 192.0 | 88.0 |
| LLDPE[1] | 10-512-1 | 30 | 0.387 | 6.28 | 2.5 | 1.3 | 0.4 |
| LLDPE[2] | 10-510-1 | 30 | 0.394 | 6.28 | 2.2 | 1.4 | 0.6 |
| HDPE[1] | 10-518-1 | 30 | 0.383 | 6.28 | 6.5 | 3.5 | 1.9 |
| HDPE[2] | 10-513-1 | 30 | 0.380 | 6.28 | 7.0 | 4.3 | 2.2 |

In a preferred embodiment, catheter shaft 12 and balloon 15 are made from any combination of PET (polyethylene teraphthalate), Nylon 12, linear low density polyethylene (LLDPE), high density polyethylene (HDPE), or other polymeric materials such as polyvinyl chloride, polyester, polyimide, polyamides, nylon, polyurethane, ethylene-propylene copolymer, ethylene-vinyl acetate copolymer, cross-linked ethylene-vinyl acetate copolymer, polyamide elastomer, and surlyn ionomer.

By selectively heating portions of catheter shaft 12, its flexibility can be increased. Importantly, its flexibility can be changed at any point along catheter shaft 12 by increasing or decreasing its temperature. For example, if it is desired to make the distal third of catheter shaft 12 more flexible than the proximal two-thirds, a heated fluid can be injected from a fluid source through heated fluid lumen 17 so that the heated fluid contacts inner lumen 13 and raises the temperature of the distal one-third of catheter shaft 12. The heated polymeric material causes the distal one-third of catheter shaft 12 to become more flexible than the proximal two-thirds of the shaft, which is the desired effect. Similarly, reducing the temperature of catheter shaft 12 will result in less flexibility (more rigid) Ports 18 in heated fluid lumen 17 allow heated fluid to flow into contact with catheter shaft 12. Polymeric plugs 19 can be located at any point along lumen 13 to block the flow of heated fluid from areas where it is undesired. The heated fluid also is withdrawn from lumen 13 through port 18.

Numerous tests were conducted on tubing material to verify increased flexibility in the heated zones. Dynamic Mechanical Analysis measurements (DMA) were conducted on tubing samples to measure the viscoelastic properties of the materials. An oscillating strain was imposed on the test specimen and the resulting stress was measured. The materials' viscoelastic properties include storage modulus (E'), loss modulus (E"), and damping modulus (Tan$^A$) Storage modulus is a measure of the amount of energy stored in the material (e.g., elasticity). Loss modulus measures the energy dissipated per unit of stored energy (E"/E'). By using the temperature ramp method, the different properties mentioned were measured as functions of temperature. Test parameters such as frequency and strain amplitude were controlled at 6.28 radian/second and 0.05%, respectively. Heating rate was maintained at 5° C./min, from 20° C. to 100° C. temperature range.

Similar results in flexibility can be achieved by heating balloon 15 with a heated fluid delivered by heated fluid lumen 17 (see FIG. 3). In prior art catheters, it is generally desired to have non-distensible balloons that are pre-shaped. With the present invention, however, it is a preferred embodiment to provide balloon 15 that is non-distensible until it is heated, at which time it will increase in diameter without a corresponding increase in pressure. Thus, in order to finish opening a coronary artery, balloon 15 is inflated with a heated fluid so that its outer diameter increases thereby further increasing the lumen (artery) opening, but without increasing balloon pressures. Such increases in balloon diameter are referred to as balloon compliance which is a measurable characteristic.

Testing was conducted on balloons made from PE 600 to measure the effects of heating the balloons to various temperatures. PE 600 is a linear low density polyethylene material (LLDPE). Five PE 600 balloons were tested at 37° C., 50° C., and 70° C. Table II details the test results of atm. versus balloon outside diameter (OD) readings for various temperatures.

TABLE II

| Atm | 37° C. OD | 50° C. OD | 70° C. OD | Overall Change in OD |
|---|---|---|---|---|
| 6 | 2.734 mm | 2.774 mm | 2.962 mm | .228 |
| 10 | 3.070 mm | 3.078 mm | 3.248 mm | .178 |
| 12 | 3.188 mm | 3.182 mm | 3.325 mm | .137 |

From the above data profile, there is a substantial change in balloon OD's at 70° C., when atmospheric pressure in the balloon is constant. Thus, there is an increase in the balloon OD's of 0.228 mm, 0.178 mm, and 0.137 mm as the temperature increases (pressure remaining constant).

Provided in Table III is the data profile of regression fit for the PE 600 balloon OD's at given temperatures and atms.

TABLE III

| Atm | 37° C. | 50° C. | 70° C. |
|---|---|---|---|
| 6 | 2.789 mm | 2.808 mm | 3.026 mm |
| 10 | 3.092 mm | 3.112 mm | 3.360 mm |
| 12 | 3.244 mm | 3.263 mm | 3.527 mm |

Other balloon materials were tested and similar results were achieved with respect to increased balloon OD's at higher temperatures. Five balloons having a surlyn ionomer composition were tested at 37° C. and 50° C. and the results are detailed in Table IV.

TABLE IV

| Atm | 37° C. OD | 50° C. OD | Overall Change in OD |
|---|---|---|---|
| 6 | 2.514 mm | 2.802 mm | .288 mm |
| 10 | 2.842 mm | 2.992 mm | .154 mm |
| 12 | 2.926 mm | 3.088 mm | .162 mm |

Table V provides the data profile of regression fit for the surlyn ionomer balloon OD's at given temperatures and atms.

TABLE V

| Atm | 37° C. | 50° C. |
|---|---|---|
| 6 | 2.557 mm | 2.848 mm |
| 10 | 2.793 mm | 3.101 mm |
| 12 | 2.911 mm | 3.228 mm |

Testing also was conducted on fine PET balloons (polyethylene teraphthalate) at 37° C. and 50° C., and the results are provided in Table VI.

TABLE VI

| Atm | 37° C. OD | 50° C. OD | Overall Change in OD |
|---|---|---|---|
| 6 | 2.782 mm | 2.806 mm | .024 mm |
| 10 | 2.858 mm | 2.880 mm | .022 mm |
| 12 | 2.880 mm | 2.902 mm | .022 mm |

Table VII provides the data profile of regression fit for the PET balloon OD's at given temperatures and atms.

TABLE VII

| Atm | 37° C. | 50° C. |
|---|---|---|
| 6 | 2.756 mm | 2.767 mm |
| 10 | 2.840 mm | 2.860 mm |
| 12 | 2.882 mm | 2.907 mm |

As can be seen by the test results, balloon diameter increased as the temperature of the PE 600 balloon material increased (while the pressure in the balloon remained constant). Importantly, the heated balloon will be more pliable as well, and when it is deflated it will more readily assume its low profile, folded configuration. A problem with some prior art balloons is that they will pancake or flatten when deflated which may result in the edges catching on the vessel walls when the catheter and balloon are withdrawn from the patient. The heated balloon 15 of the present invention, however, will readily deflate and assume its folded profile so that it may be more easily withdrawn from the patient.

As with catheter shaft 12, a decrease in flexibility (higher stiffness) in the balloon can be achieved by cooling it, with, for example, a cooling fluid. A cooling fluid would provide higher rupture strength during inflation, but would decrease flexibility and folding characteristics during deflation. Cooling fluid can be provided to balloon 15 in much the same manner as described for providing heating fluid.

Figure 5:
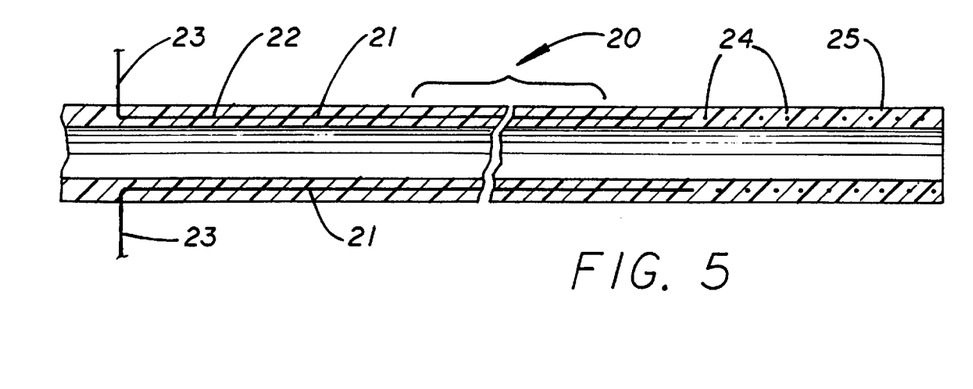
FIG. 5 is an enlarged, longitudinal, cross-sectional view of a catheter device according to an alternative embodiment the present invention.

In another embodiment, FIG. 5 illustrates a catheter 20 according to the present invention. Such catheter is advanceable along a previously emplaced guidewire to the operative site within a patient's vascular system. The catheter is formed of material that becomes substantially more flexible as its temperature is increased above the patient's ambient temperature (nominally 98.6° F. or 37° C.) to a temperature of 60° C. which has been found to be tolerable within the body for limited periods of time. In the embodiment illustrated in FIG. 5, an electrical conductor 21 is incorporated in the catheter wall 22. The two leads 23 of the conductor are inter-connectable to a power supply (not shown) near the catheter's proximal end and are linked to resistance wiring 24 coiled about distal end 25. Passing electric current through the wiring causes the temperature of the distal end to rise at a very controllable and predictable rate resulting in an increase in the flexibility of the distal end 25.

In use, the catheter 20 is advanced along an emplaced guidewire until its progress is impeded by an excessively tight bend in the guidewire. In order to facilitate further progress and prevent injury to the vessel walls, an electric current is passed through conductor 21 and resistance wiring 24 in order to increase the operating temperature of the distal end 25 and hence its flexibility. Once past the tight bend, the temperature of the distal end is reduced by decreasing power, which should correspondingly provide greater stiffness (less flexibility) to catheter 20.

Figure 6:
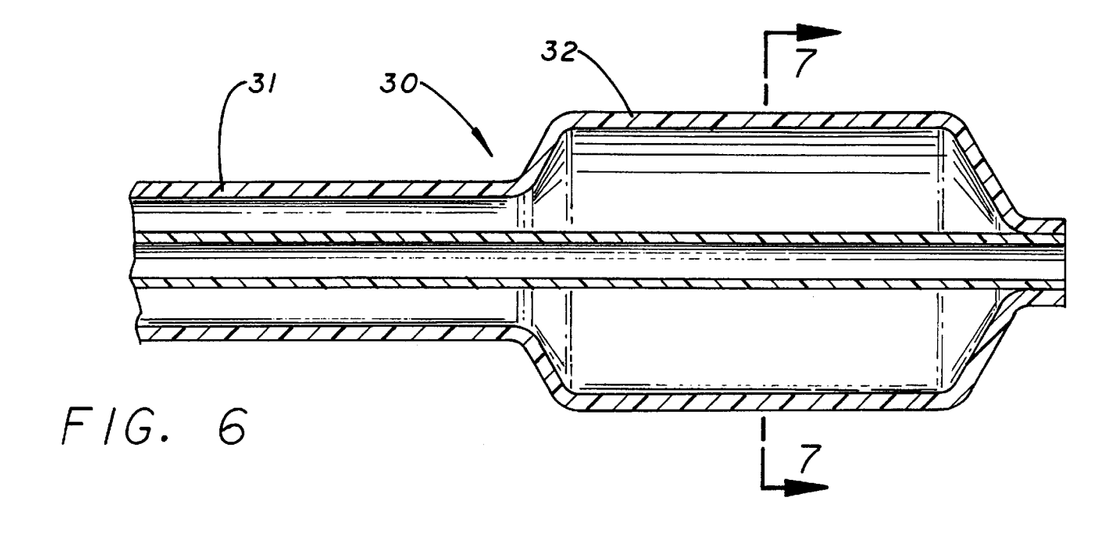
FIG. 6 is an enlarged cross-sectional view of the balloon portion of the catheter.

FIG. 6 illustrates a balloon-type dilatation catheter 30. The device consists of a multiple lumen catheter body 31 having an inflatable balloon 32 near its distal end. While the balloon is in its collapsed state, the device is advanceable along a previously emplaced guidewire to the operative site. Dilatation of the targeted artery is accomplished upon inflation of the balloon via fluid pumped through one of the lumens. Deflation of the balloon at the conclusion of the operation allows the device to be withdrawn.

Figure 7:
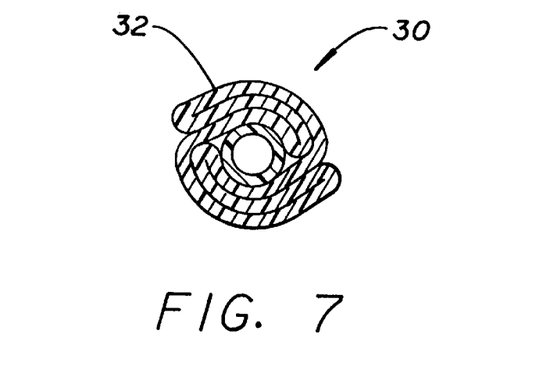
FIG. 7 is a cross-sectional view taken along lines 7—7 of FIG. 6 depicting the balloon in its folded state.

The catheter 30 shown in FIG. 6 is heated with the introduction of heated fluid just prior to the final deflation and withdrawal. The balloon 32 may be made of a material which is affected by changes in its operating temperature, for example cross-linked polymers or thermoplastics such as PET (polyethylene teraphthalate). The heated fluid serves to transfer heat to the balloon 32 which in turn renders the balloon more pliable and therefore more readily disposed to reassume its folded shape (FIG. 7). In the event enhanced rupture strength is required during dilatation, the balloon is expanded with cooled fluid.

Figure 8:
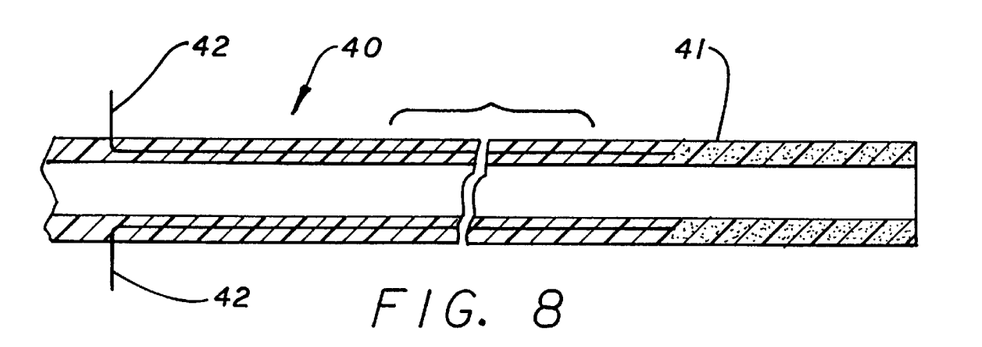
FIG. 8 is an enlarged longitudinal cross-sectional view of another embodiment of the catheter device.

FIG. 8 illustrates another alternative embodiment of a catheter 40. The distal end 41 of the surgical device is formed of material that becomes more flexible with an increase in temperature. Moreover, the material is selected to absorb light energy at a preselected wavelength. One or more optical fibers 42 are incorporated in the catheter wall to conduct light of the preselected wavelength from a laser (not shown) to the distal end 41 of the catheter 40. Energization of the laser causes the distal end 41 to heat up and become more flexible as previously described.

Figure 9:
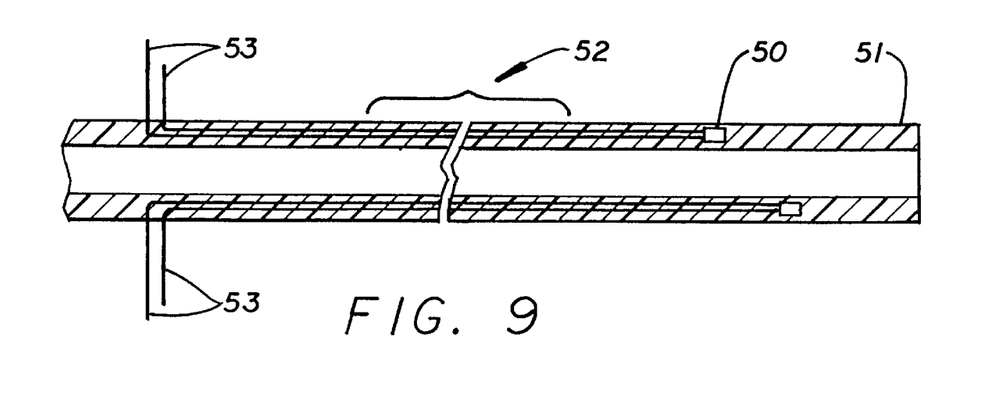
FIG. 9 is an enlarged longitudinal cross-sectional view of an alternative embodiment of the catheter device.

FIG. 9 illustrates an alternative embodiment wherein a plurality of Peltier-type devices 50 are incorporated near distal end 51 of a catheter 52. By energizing leads 53 with the appropriate voltage and polarity, the distal end 51 of the catheter is cooled. In use, when an increase in stiffness is necessary, as for example when it is necessary to push the catheter 52 through an occlusion in an artery, the Peltier-type devices 50 are energized to quickly and predictably lower the temperature and increase stiffness. Temperatures near 0° C. are tolerable within the vascular system for brief periods of time.

While a particular form of the invention has been illustrated and described, it will also be apparent to those skilled in the art that various modifications can be made without departing from the spirit and scope of the invention. For example, a wide variety of materials will be adaptable for use in devices according to the present invention. Additionally, many different methods can be employed to bring about an increase or a decrease of the surgical device's operating temperature. Furthermore, it is not intended that the present invention be limited to the heating or cooling of the distal end of the various angioplastic surgical devices, as other regions of such devices may benefit from a change in their mechanical properties as brought about by the heating or cooling thereof. Accordingly, it is not intended that the invention be limited except as by the appended claims.

What is claimed is:

1. A medical device for insertion into and transport through a patient's vascular system, comprising:
   an elongate member including a shaft, said shaft having a selected region formed of material having mechanical properties subject to change upon variation of said material's operating temperature; and
   means for communicating a temperature controlled fluid to the selected region of said shaft for varying the selected region's operating temperature without varying the operating temperature of an unselected region of the shaft of the elongate member, whereby the mechanical properties of the selected region of the shaft can be changed without changing the mechanical properties of the unselected region of the shaft of the elongate member.

2. The device of claim 1, wherein said control means includes heating means for increasing the operating temperature of the selected region of said elongate member.

3. The device of claim 1, wherein said elongate member further comprises a dilatation catheter having a balloon portion on a distal end of said shaft, said balloon portion becoming more flexible upon application of a heated fluid to raise the temperature of said balloon portion.

4. The device of claim 1, wherein said elongate member is formed from a polymeric material taken from the group of polymeric materials including linear low density polyethylene, high density polyethylene, polyethylene, polypropylene, polyethylene teraphthalate (PET), polyolefins, polyvinyl chloride, polyester, polyimide, polyamides, nylon, polyurethane, ethylene-propylene copolymer, ethylene-vinyl acetate copolymer, cross-linked ethylene-vinyl acetate copolymer, polyamide elastomer, and surlyn ionomer.

5. The device of claim 1, wherein said control means for controllably varying the selected region's operating temperature includes controlling temperature in the range of 0° C. to 70° C.

6. A dilatation catheter system, comprising:
   a shaft having a proximal end and a distal end formed of a material which becomes increasingly flexible as its operating temperature is increased; and
   control means for communicating a temperature controlled fluid to the distal end of the shaft for increasing the temperature of said distal end without increasing the temperature of the proximal end of the shaft whereby the distal end can be made increasingly flexible by increasing the temperature of the distal end of the shaft, without increasing the flexibility of the proximal end of the shaft.

7. The dilatation catheter of claim 6, wherein said distal end further comprises a balloon portion having increasing flexibility as its temperature is increased by said heated fluid.

8. The dilatation catheter of claim 7, wherein said balloon portion increases in diameter in the range of 3% to 10%.

9. The dilatation catheter of claim 6, wherein said distal end of said catheter is formed from a polymeric material taken from the group of polymeric materials including linear low density polyethylene, high density polyethylene, polyethylene, polypropylene, polyethylene teraphthalate (PET), polyolefins, polyvinyl chloride, polyester, polyimide, polyamides, nylon, polyurethane, ethylene-propylene copolymer, ethylene-vinyl acetate copolymer, cross-linked ethylene-vinyl acetate copolymer, polyamide elastomer, and surlyn ionomer.

10. A balloon catheter system for insertion into and transport through a patient's vascular system, comprising:
    an elongate tubular member having a proximal portion and a distal portion;
    an inflatable member carried by the distal portion of elongate tubular member, said inflatable member being formed of polymeric material which permits said inflatable member to assume an increasingly tightly folded configuration as its temperature is increased and increased rupture strength as its temperature is decreased; and
    control means for introducing temperature controlled fluid into the distal portion of said elongate tubular member and said inflatable member for varying the temperature of said distal portion of said elongate tubular member and said inflatable member without varying the temperature of said proximal portion of the elongate tubular member.

11. A method for varying the flexibility of a catheter, said device having an elongate member having a shaft having a selected region formed of a material having mechanical properties subject to change upon variation of said material's operating temperature by a control means, the method comprising:
    introducing said elongate member into the vasculature of the patient;
    transporting said elongate member through the vasculature; and
    communicating a temperature controlled fluid to the selected region of the shaft of the elongate member for varying the temperature of said selected region of the shaft of the elongate member without varying the temperature of an unselected region of the shaft of the elongate member to change the flexibility of said selected region without changing the flexibility of the unselected region.

12. The method of claim 11, wherein said control means includes heating means for increasing the operating temperature of said selected region of said elongate member.

13. The method of claim 12, wherein said heating means includes means for heating a fluid to a temperature in the range of 20° C. to 70° C.

14. A medical device for insertion into and transport through a patient's vascular system, comprising:
    an elongate member formed of material having mechanical properties subject to change upon variation of the temperature of the material, said elongate member having a shaft with a proximal portion and a distal portion;
    means for communicating a temperature controlled fluid to a selected portion of the shaft of the elongate member for varying the temperature of the selected portion of the shaft of said elongate member without varying the temperature of an unselected portion of the shaft of said elongate member, whereby the mechanical properties of the selected portion of the shaft of said elongate member can be changed without changing the mechanical properties of the unselected portion of the shaft of said elongate member.

15. The mechanical device of claim 14, wherein said shaft has a first lumen extending therethrough, and said means for varying temperature comprises a second lumen extending through said first lumen, said first lumen having a proximal portion and a distal portion separated from said proximal portion by a plug, said second lumen being in fluid communication with a source of temperature controlled fluid, and said second lumen extending through said proximal portion, through said plug to said distal portion for communicating said temperature controlled fluid to said distal portion for varying the temperature of said distal portion without varying the temperature of said proximal portion.

16. The medical device of claim 15, wherein said distal portion carries a balloon, said second lumen being in fluid communication with said balloon for communicating said temperature controlled fluid to said balloon for varying the temperature of said balloon.

* * * * *

UNITED STATES PATENT AND TRADEMARK OFFICE
CERTIFICATE OF CORRECTION

PATENT NO. : 5,853,408
DATED : Dec. 29, 1998
INVENTOR(S) : Ketan P. Muni

It is certified that error appears in the above-identified patent and that said Letters Patent is hereby corrected as shown below:

Column 9, claim 1, line 22, before "means", add --control--.

Signed and Sealed this

Sixth Day of April, 1999

Attest:

Q. TODD DICKINSON

*Attesting Officer*     *Acting Commissioner of Patents and Trademarks*